United States Patent [19]

Fukazawa et al.

[11] Patent Number: 5,074,668

[45] Date of Patent: Dec. 24, 1991

[54] SURFACE INSPECTION APPARATUS

[75] Inventors: Chiaki Fukazawa, Urawa; Kenji Aizawa, Fuchu, both of Japan

[73] Assignee: Kabushiki Kaisha Toshiba, Kawasaki, Japan

[21] Appl. No.: 409,073

[22] Filed: Sep. 19, 1989

[30] Foreign Application Priority Data

Sep. 20, 1988 [JP] Japan ............................ 63-233647

[51] Int. Cl.$^5$ .................... G01N 21/84; G01N 21/88
[52] U.S. Cl. .................... 356/429; 356/431; 356/445; 250/572
[58] Field of Search .................... 356/429-431, 356/445, 448, 380, 385, 237, 446; 250/571-572, 563

[56] References Cited

U.S. PATENT DOCUMENTS

| | | | |
|---|---|---|---|
| 3,612,702 | 10/1971 | Troll | 356/430 |
| 3,663,107 | 5/1972 | Denis et al. | 356/445 |
| 4,260,899 | 4/1981 | Baker | 250/563 |
| 4,277,178 | 7/1981 | Cushing et al. | 356/431 |
| 4,488,808 | 12/1984 | Kato | 356/73 |
| 4,500,208 | 2/1985 | Sick | 356/431 |
| 4,522,497 | 6/1985 | Ikin | 356/431 |
| 4,591,726 | 5/1986 | Schenk | 356/431 |
| 4,868,403 | 9/1989 | Takahashi et al. | 356/431 |

*Primary Examiner*—Richard A. Rosenberger
*Assistant Examiner*—Hoa Pham
*Attorney, Agent, or Firm*—Foley & Lardner

[57] ABSTRACT

A surface inspection apparatus used for inspecting defects of sheet material surfaces includes an optical scanner, a lens unit, a filter, and a photoelectric converter. The lens unit has a plurality of convex lenses arranged in the scanning direction of the optical scanner and adjoining each other. Partitions are arranged in the direction perpendicular to the direction of arrangement of the convex lenses, extending from both ends of the lens unit and from the adjoining portions between the adjoining convex lenses towards the filter.

10 Claims, 11 Drawing Sheets

SURFACE INSPECTION APPARATUS

FIELD OF THE INVENTION

This invention relates to a surface inspection apparatus for inspecting defects of the surface of sheet materials by using diffracted light of laser beams.

BACKGROUND OF THE INVENTION

Figure 16A:
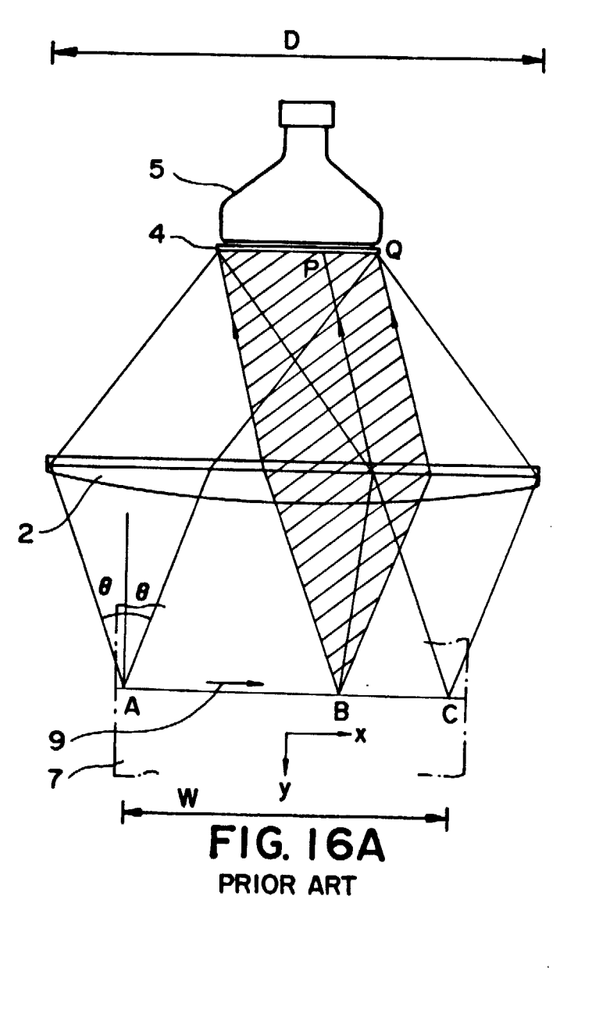
FIGS. 16A and 16B illustrate a conventional surface inspection apparatus.
Figure 16B:
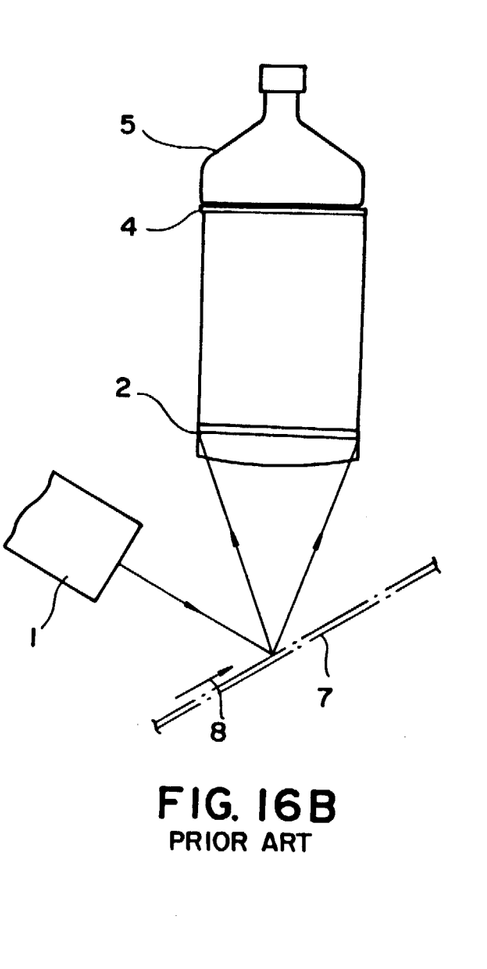

FIGS. 16A and 16B show an example of a conventional surface inspection apparatus (as disclosed, for example, in Japanese patent publication No. 52-21387).

In FIGS. 16A and 16B, on the upper left side of an inspected object or a sheet material 7 moved in the direction of an arrow 8 by means of a drive mechanism (not shown) is disposed an optical scanner 1. The optical scanner 1 is moved in the perpendicular direction 9 to the moving direction 8 of the sheet material 7 and in the direction parallel to the sheet material 7 by means of a mover mechanism (not shown), and irradiates laser light (hereinafter "light") towards the surface of the sheet material 7. On the upper right side of the sheet material 7, a convex lens 2 which receives reflected light from the surface of the sheet 7 and sends transmitted light therethrough to a spatial filter 4 above the convex lens 2, is arranged in the direction perpendicular to the ray axis of the reflected light and in the direction parallel to the sheet material 7. The light transmitted through the spatial filter 4 is transmitted to a signal processor (not shown) via a photomultiplier 5, so that the changes of diffraction patterns caused by defects of the surface of the sheet material are detected. This apparatus which uses the spatial filter 4 in accordance with the patterns of the textures or defects of the sheet material surface, enables surface inspection that more closely approximates human viewing than other apparatuses which detect only simple changes of reflected light quantities.

However, in this apparatus the scanning width cannot be made larger (the limit of the width is 200~300 mm) because the inspection precision will deteriorate and so it is necessary to arrange a plurality of apparatus side by side in order to inspect wide sheet materials 7.

It is also necessary to arrange a plurality of photomultipliers at the position of the spatial filter in order to separately detect the components of the diffraction light and to distinguish the classifications of the surface defects. These mechanisms are required for each apparatus because stationary diffraction patterns must be formed as the light diffracted from each scanning point of the surface of the sheet material in same direction with respect to the surface, must be converged to the same point of the spatial filter when the light moves in the direction of arrow 9 as shown in FIGS. 16A and 16B.

The following equation holds when it is supposed that the diffraction angle of light to be converged is $\theta$, the distance between the scanning surface and the convex lens 2 is h, the focal length of the convex lens 2 is , the scanning width is W, and the aperture of the convex lens 2 is D.

$$\frac{f}{D} = \frac{f}{W + 2h \cdot \tan \theta}$$

In this equation, if the scanning width is increased, a convex lens which has a small aperture ratio $f/D$ is required. However, there is a limitation with respect to the aperture ratio and the scanning width is restricted as a consequence.

SUMMARY OF THE INVENTION

Accordingly, it is an object of this invention to provide a surface inspection apparatus which facilitates surface inspection of wide sheets of material.

The foregoing object is accomplished by providing a surface inspection apparatus, comprising an optical scanner that irradiates laser light towards an inspected object surface, a lens converging diffraction light from the surface and having a plurality of convex lenses arranged in the scanning direction of the optical scanner and adjoining each other, a filter filtering the diffraction light converged by the lens, a photoelectric converter converting the diffraction light through the filter into electrical signals, and partitions that shut out the diffraction light and arranged in the direction perpendicular to the direction of arrangement of the convex lenses and extending from both ends of the lens and from the adjoining portions between the convex lenses towards the filter means.

BRIEF DESCRIPTION OF THE DRAWINGS

The invention is illustrated diagrammatically in the following drawings wherein.

DESCRIPTION OF THE PREFERRED EMBODIMENT

Preferred embodiments of the surface inspection apparatus of this invention are shown in drawings, in which the parts shown in FIGS. 16A and 16B are omitted.

Figure 1A:
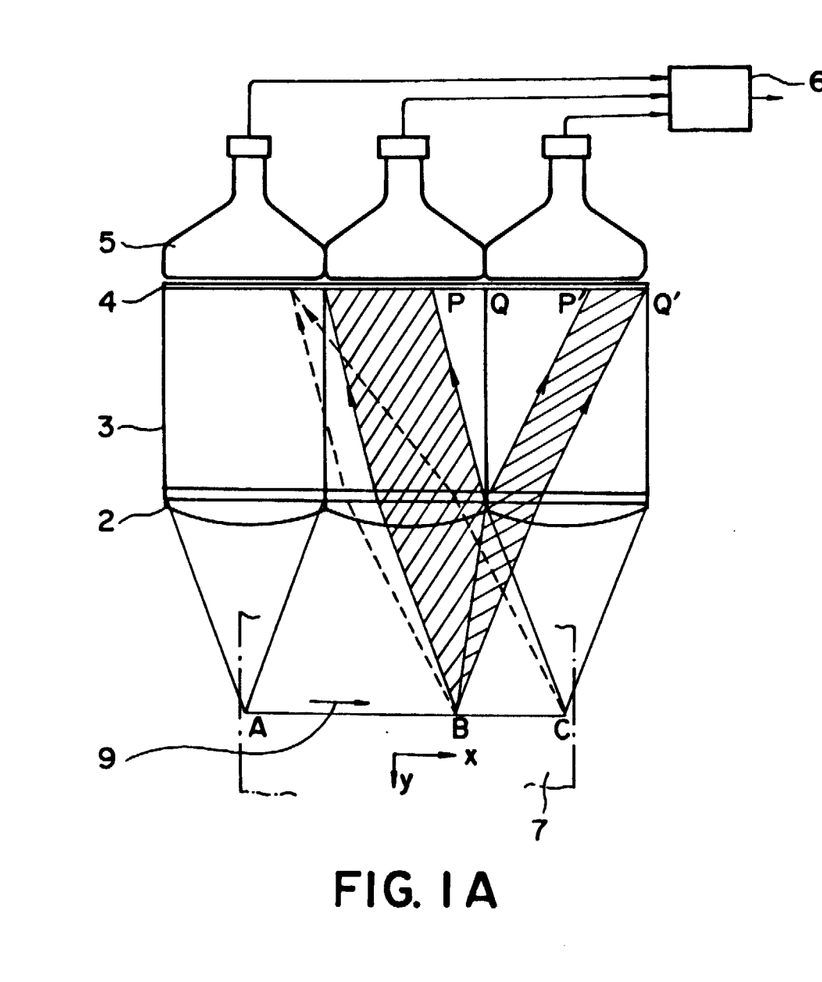
FIGS. 1A and 1B illustrate an embodiment of the surface inspection apparatus of this invention.
Figure 1B:
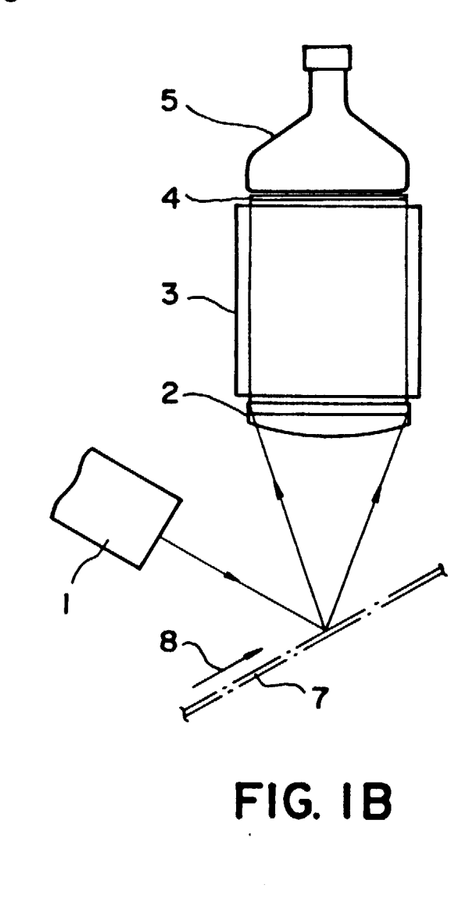

In FIGS. 1A and 1B, on the upper right side of a sheet material 7, a plurality of convex lenses 2 which receive reflected light from the surface of the sheet material 7, are arranged side by side. The reflected light is generated by light irradiated in the direction perpendicular to an arrow 9 from an optical scanner 1 which moves in the direction of the arrow 9. A plurality of spatial filters 4 which filter light converged by the convex lenses 2 are also arranged side by side above and in parallel to the convex lenses 2. Each spatial filter 4 corresponds to each convex lens 2. Partitions 3 are vertically arranged, and extending from the adjoining portions between the adjoining spatial filters 4 towards the adjoining portions between the adjoining convex lenses 2, and from both ends of the spatial filters 4 towards both ends of the convex lenses 2. The partitions 3 which neither reflect nor transmit light are a little wider than the spatial filters 4 and the convex lenses 2.

Furthermore, above each spatial filter 4 are disposed photomultipliers 5 corresponding to each spatial filter 4, and the output sides of the photomultipliers 5 are connected to an adder 6 of a signal processor (not shown).

Figure 2:
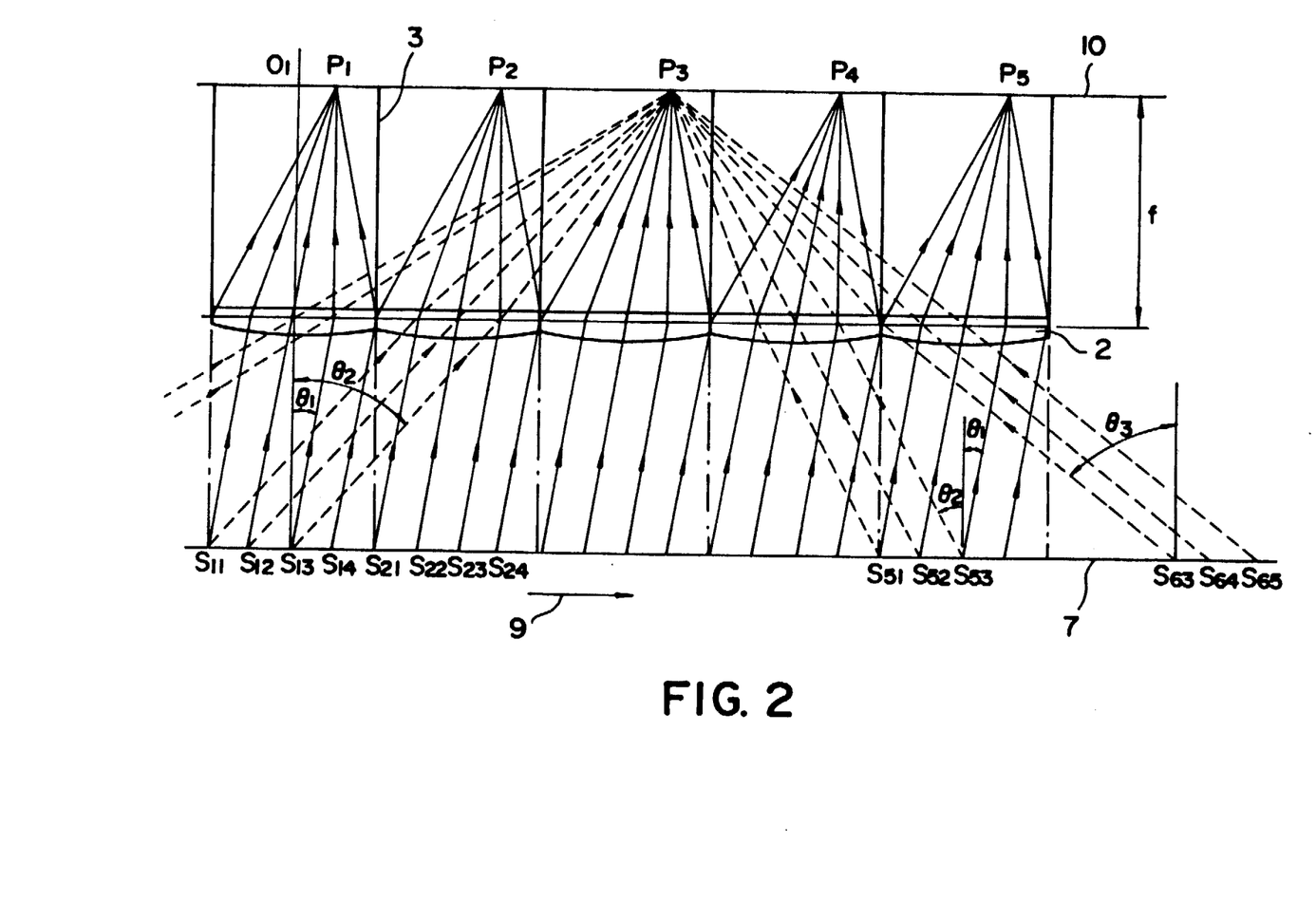
FIGS. 2~4 illustrate an operation of the surface inspection apparatus of this invention.
Figure 3:
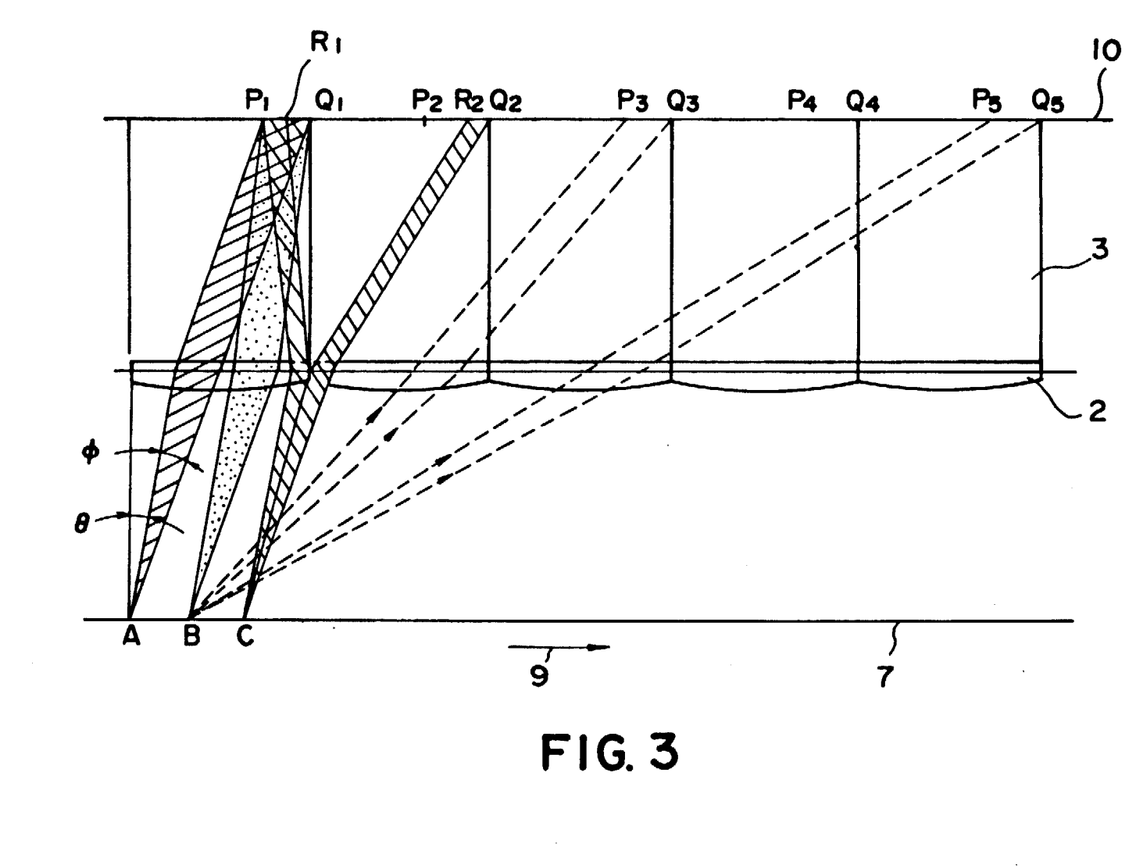

In this surface inspection apparatus, when light from the optical scanner 1 moving in the direction of the arrow 9 is irradiated in the direction perpendicular to the arrow 9 towards the surface of the sheet material, the reflected light shown with broken lines in FIGS. 1~3 is not transmitted through the partitions 3 (namely, the light transmitted through one convex lens 2 does not enter the focal planes corresponding to the other convex lenses 2).

As a result, the incident light upon one point of each focal plane is only diffraction light in one direction with respect to the inspected sheet material 7. This phenomenon has nothing to do with the scanning position, and diffraction patterns similar to the stationary diffraction patterns by one lens are obtained.

Namely, in FIG. 2 illustrating the operation of the surface inspection apparatus of this invention, the diffracted light at the diffraction angle $\theta_1$ with respect to the direction of light reflected to the right (O order diffraction direction) is from the left end $S_{11}$ to $S_{14}$ converged to a point $P_1$ of the focal plane 10. The light from over $S_{14}$ to $S_{24}$ is converged by the next convex lens 2 to the next point $P_2$. Thus, the diffraction light at the same diffraction angle from the surface of the sheet material 7 is converged at the corresponding point on the focal plane of each convex lens (namely, at the point which corresponds to each other when the focal planes of each convex lens is laid one upon another). Accordingly, when the corresponding point on the focal plane of each convex lens is identified, the same diffraction pattern as the conventional one using one lens as in FIGS. 16A and 16B is obtained.

Furthermore, taking note of, for example a point $P_3$, reflected light from the sheet material 7 at the diffraction angle $\theta_2$ or $\theta_3$ with respect to the direction of light reflected to the right, would reach the point $P_3$ as shown in broken lines if it was not for the partitions 3. As mentioned above, the partitions 3 shut out the light shown by broken lines, so that the incident light upon one point of the focal plane of each convex lens 2 is limited to the diffraction light in one direction from the inspected sheet material 7.

Next, FIG. 3 shows how the light at diffraction angles between $\theta$ and $\theta + \phi$ are converged with respect to the O order diffraction direction when the scanning position is moved.

In FIG. 3, the light at the diffraction angles between $\theta$ and $\theta + \phi$ reflected from points A, B is converged to points between $P_1$ and $Q_1$ on the focal plane. As for a point C, a part of the light from the point C is converged to points between points $P_1$ and $R_1$ on the focal plane of first convex lens 2, and another part of light from the point C is converged to points between points $R_2$ and $Q_2$ on the focal plane of second convex lens 2. In FIG. 3, points $P_1$, $Q_1$, and $R_1$ of the first convex lens correspond to points $P_2$, $Q_2$ and $R_2$ of the second convex lens respectively. Accordingly, the diffraction light extending from the first convex lens to the second convex lens is mutually supplemented and eventually this light is identified as the light gathering from point $P_1$ to point $Q_1$ or from point $P_2$ to $Q_2$. Accordingly, the diffraction light at the diffraction angle between $\theta$ and $\theta + \phi$ may be gathered by gathering the incident light upon the points between point $P_i$ and point $Q_i$ on the corresponding focal plane of each convex lens (Note: the diffraction light to the directions shown by broken lines does not enter points between point $P_i$ and point $Q_i$ because it is shut out by the partitions 3). In FIG. 3, the letter i corresponds with the reference number of each convex lens 2.

In the drawings accompanying the specification of this invention, the convex lenses 2 are assumed to have one main plane and no astigmatism.

In FIG. 1, each spatial filter 4 is on the corresponding focal plane of each convex lens, and the transmittances within the spatial filters 4 are changed. The transmission light through the spatial filters 4 enter the photomultipliers 5 corresponding to each convex lens 2. Moreover, the spatial filters 4 control the quantities of the light entering the photomultipliers 5 according to the angles of diffraction, namely the spatial filters 4 filter the light with respect to the spatial frequencies of the light.

Figure 4:
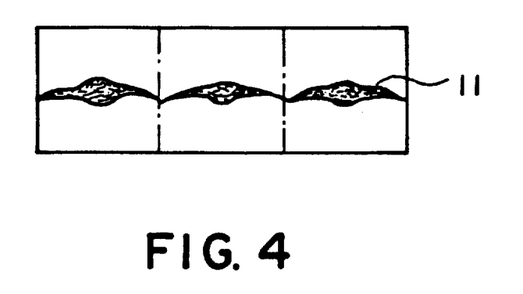

For example, when the negative film of diffraction pattern 11 (in FIG. 4) in accordance with the textures of the surface of the sheet material 7 is assumed to be a spatial filter, the different portions of the diffraction pattern in accordance with the defects of the surface are introduced into the photomultipliers 5 and become electrical signals caused by the defects of the surface of the sheet material 7.

Figures 5A, 5B:
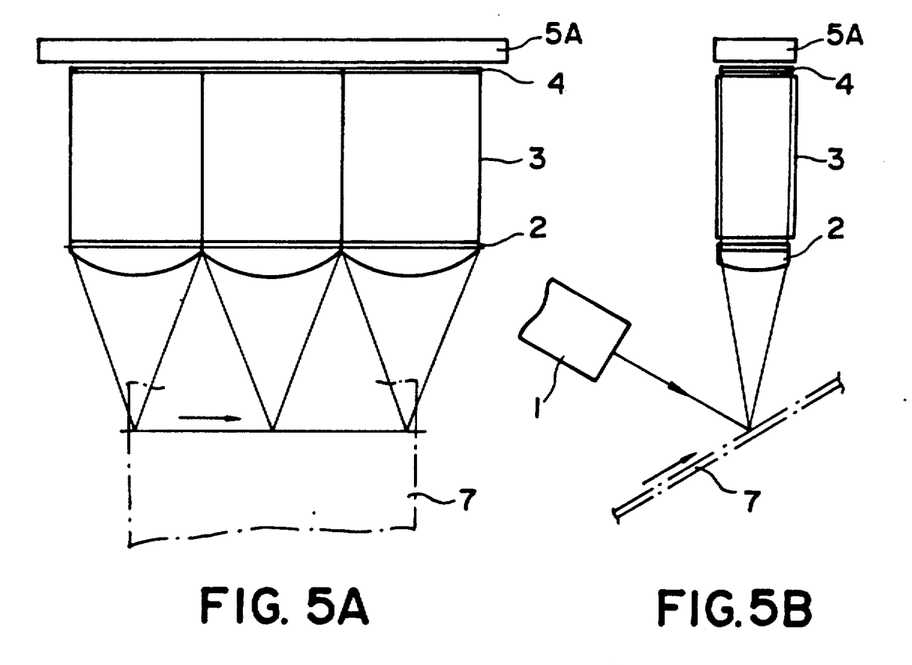
FIGS. 5~15 illustrate other embodiments of the surface inspection apparatus of this invention.

FIGS. 5A and 5B show another embodiment of the surface inspection apparatus of this invention.

In FIGS. 5A and 5B, a plane semiconductor optical sensor 5A having a rectangular receiving light surface is arranged as a photoelectric converter above the spatial filters 4. In this case, as the transmission light through a plurality of spatial filters 4 are converted into electrical signals by only one optical sensor 5A, the adder 6 is unnecessary, and the height of the apparatus of this invention may be decreased.

Figures 6A, 6B:
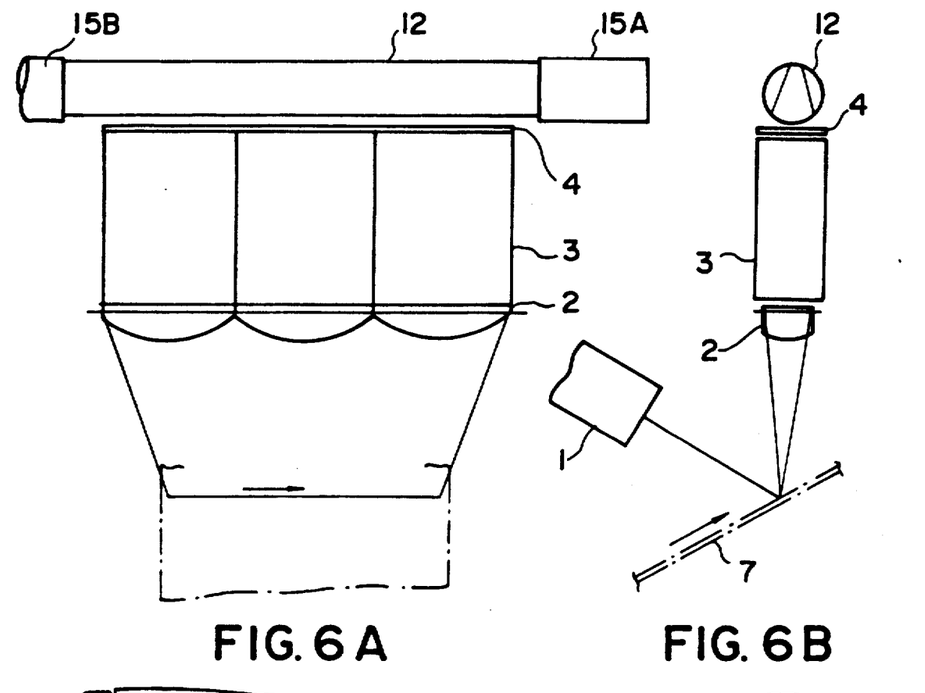

FIGS. 6A and 6B show a further embodiment of the surface inspection apparatus of this invention. In FIGS. 6A and 6B, a light guide 12 is arranged above the spatial filters 4, and a pair of photomultipliers 15A, 15B are connected to the left and right ends of the light guide 12.

In this case, the same advantages as in FIGS. 5A and 5B are obtained. In addition, high speed scanning is possible by using the photomultipliers 15A, 15B which respond rapidly so that the surface inspection of the sheet material on the high speed line can be performed easily.

Figure 7A:
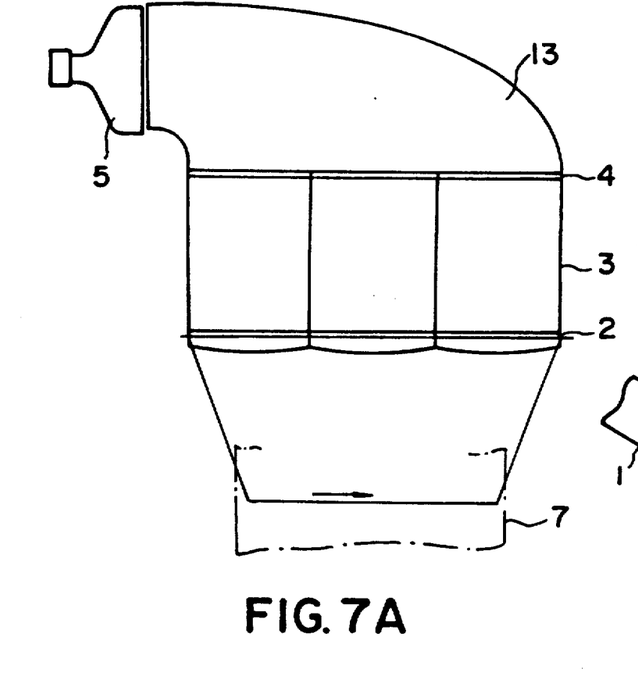
Figure 7B:
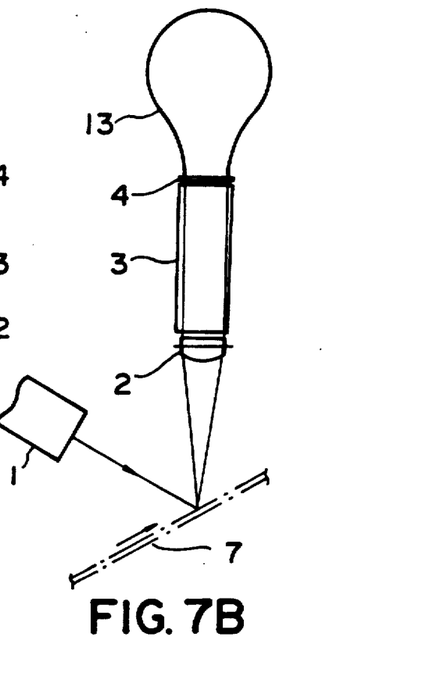

FIGS. 7A and 7B show a further embodiment of the surface inspection apparatus of this invention. In FIGS. 7A and 7B, the lower end of a bundle fiber 13 is disposed above the spatial filters 4, and the upper end of the handle fiber 13 is connected to the photomultiplier 5.

In this case, the same advantages as in FIGS. 6A and 6B are obtained, and in addition, the position of the photomultiplier 5 can be freely chosen.

Figures 8A, 8B:
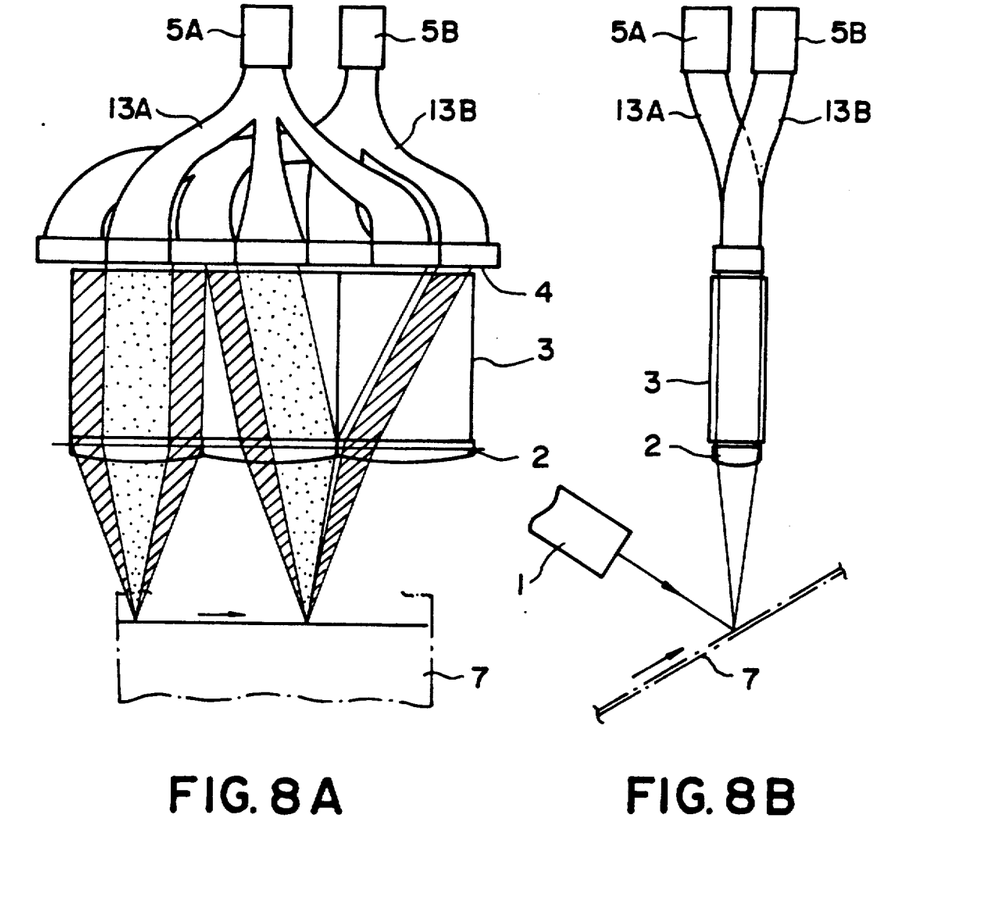

FIGS. 8A and 8B show a further embodiment of the surface inspection apparatus of this invention. In FIGS. 8A and 8B, a pair of bundle fibers 13A, 13B whose lower ends have a plurality of optical introduction openings are arranged above the spatial filters 4. The upper ends of the bundle fibers 13A, 13B are connected to the photomultipliers 5A, 5B respectively. The optical introduction openings of each handle fiber are arranged at the position where the desirable components of diffraction light on the focal plane of each convex lens 2 reach, so that O-order diffraction light and the light thereabouts shown as the dotted area and the other light shown as the shaded area are caught and bundled separately.

In this case, as the outputs of the photomultipliers 5A, 5B correspond to the changes of two different diffraction light components, the features of the surface defects may be inspected by analyzing these outputs.

Furthermore, more than two different diffraction light components may be detected separately by increasing the number of the handle fibers. A space filter is not necessary in this case.

Figures 9A, 9B:
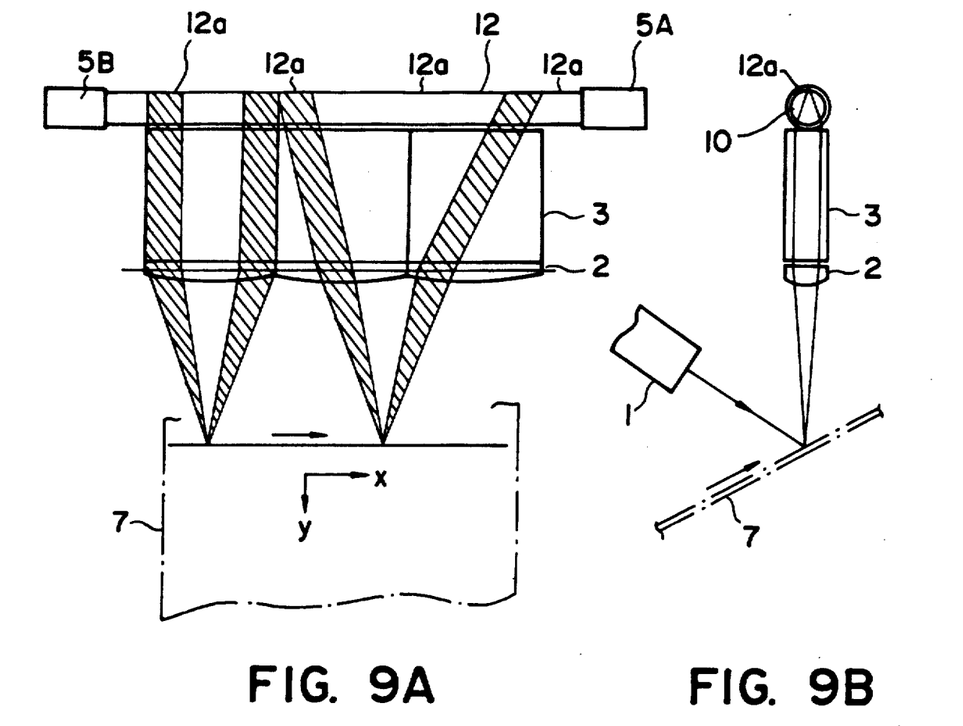

FIGS. 9A and 9B show a further embodiment of the surface inspection apparatus of this invention. In FIGS. 9A and 9B, the light guide 12 whose upper end is placed on the focal plane, is arranged horizontally above the convex lenses 2, and light diffusion portions 12a are formed at the only surface portions of the light guide 12 where desirable diffraction light components reach, as shown by the shaded portion. The light guide 12 introduces the light diffused by light diffusion portions 12a to the photomultipliers 5A, 5B at the left and right end of the light guide 12, and the equivalent of a band pass filter is formed thereby.

Figure 10A:
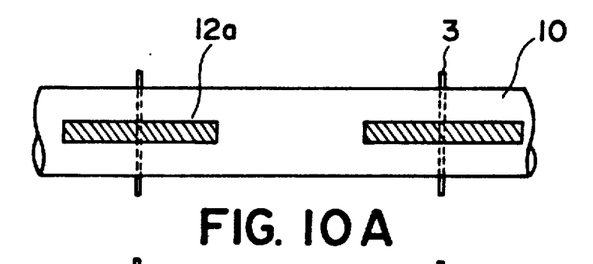
Figure 10B:
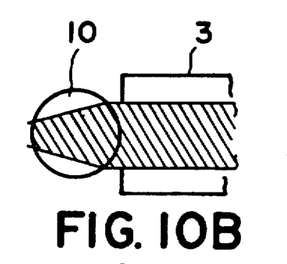

FIG. 10A is an enlarged plan view of the light diffusion portions 12a in FIG. 9A, and FIG. 10B is a right side view of FIG. 10A.

Figure 10C:
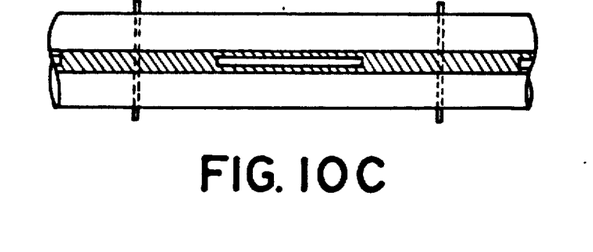
Figure 10D:
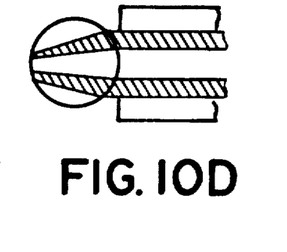

FIGS. 10C and 10D show the light guide which has an area in which a light diffusion portion exists and an area in which a light diffusing portion does not exist, in the direction perpendicular to the axis of the light guide 12. As a result, the band pass filter with a spatial frequency in the Y direction (in the sheet material moving direction) is also formed.

Figures 11A, 11B:
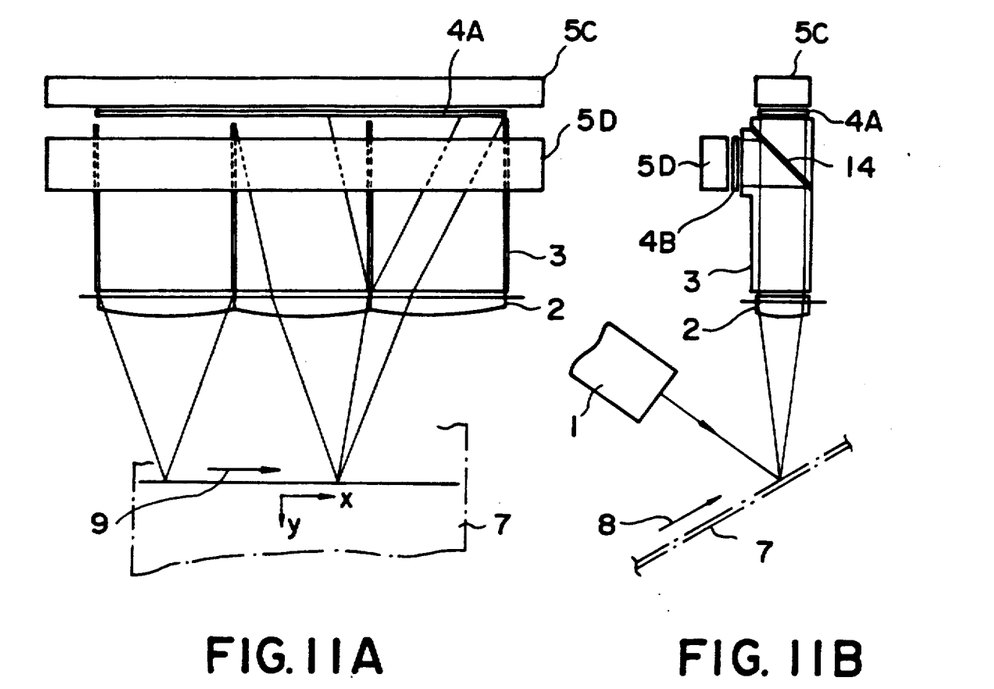

FIGS. 11A and 11B show a further embodiment of the surface inspection apparatus of this invention. In FIGS. 11A and 11B, semi-transparent mirrors 14 are arranged between each convex lens 2 and corresponding space filter 4. The transmission light through the semi-transparent mirrors 14 is introduced to the above spatial filters 4A and the light reflected from the semi-transparent mirrors 14 is introduced to the spatial filters 4B in front of the semi-transparent mirrors 14 and this light is converted into electrical signals by plane photoelectric converters 5C, 5D at the end portions of these spatial filters 4A, 4B respectively. Accordingly, the classification of the defects of the surface of the sheet material is easily made by using two kinds of spatial filtering.

Figure 12A:
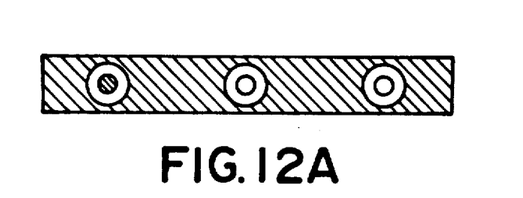
Figure 12B:
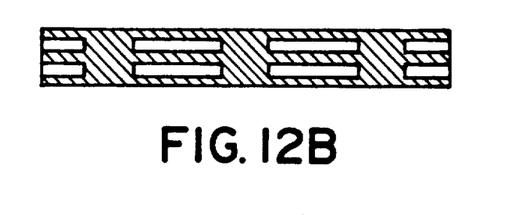

FIGS. 12A and 12B show the example of the above mentioned two kinds of spatial filters, wherein FIG. 12A shows a first spatial filter which gathers the diffraction light around O-order diffraction light, and FIG. 12B shows a second spatial filter which gathers diffraction light in the X axis direction except for O-order diffraction light and the light thereabouts in the Y direction.

Figure 13A:
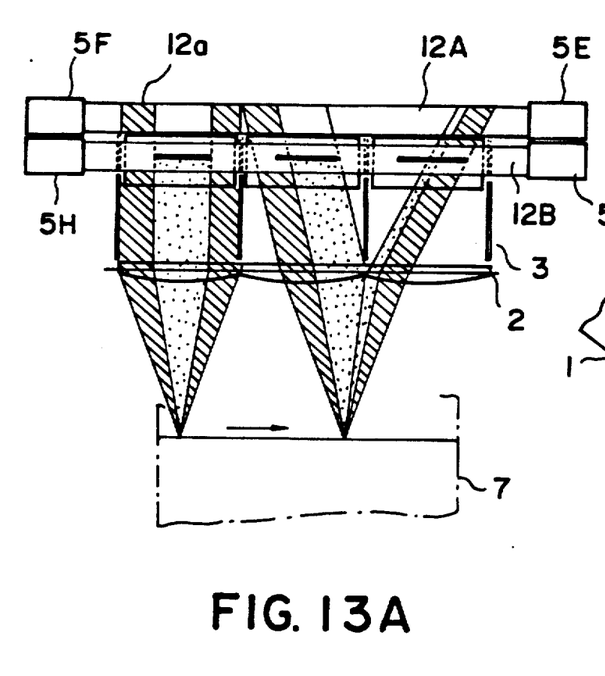
Figure 13B:
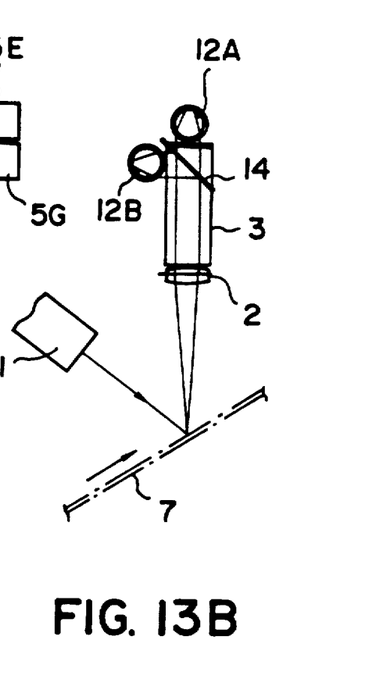

FIGS. 13A and 13B show a further embodiment of the surface inspection apparatus of this invention. In FIGS. 13A and 13B, a pair of light guides 12A and 12B are arranged above and in front of the semi-transparent mirrors 14 shown in FIGS. 12A and 12B respectively. The light guide 12B is arranged so that its front surface is placed at a position corresponding to the focal plane of the convex lenses 2. In this case, which is similar to that shown in FIGS. 9A and 9B, the light diffusion portions are on the surface portions of the light guide 12A, 12B where desirable diffraction light components reach, so that the equivalent of a band pass filter is formed.

Figures 14A, 14B:
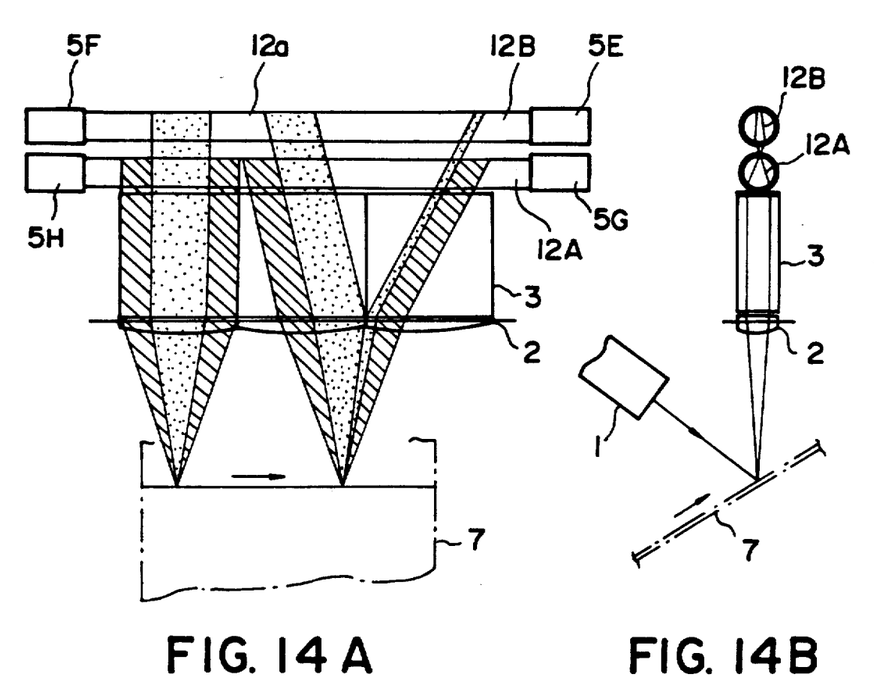

FIGS. 14A and 14B show a further embodiment of the surface inspection apparatus of this invention. In FIGS. 14A and 14B, the light guide 12A is horizontally disposed above the convex lenses 2 so that its upper end is placed on the focal plane of the convex lenses 2, and the light guide 12B is further arranged above and parallel to the light guide 12A.

In this case, only the portions of the light guide 12A where special components of diffraction light reaching it are diffusible, the diffusion light therefrom is introduced to photoelectric converters 5H, 5G at the left and right ends of the light guide 12A. In FIG. 14A, only the diffraction light shown shaded is converged.

Furthermore, the light guide 12B gathers the transmission light through the light guide 12A and introduces the light to photoelectric converters 5E, 5F at the left and right ends of the light guide 12B. As a result, the two different components of the diffraction light are separately gathered and converted into electrical signals by photoelectric converters 5E~5H.

Figure 15:
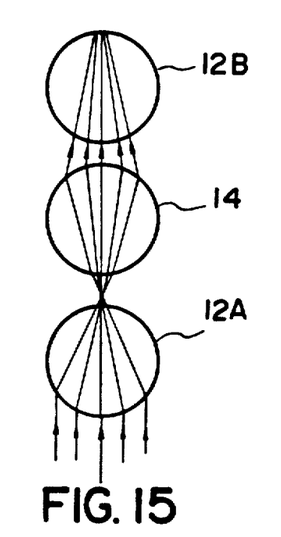

FIG. 15 shows a further embodiment of the surface inspection apparatus of this invention. In FIG. 15, a transparent pole 14 made of acrylic resin is arranged between the light guides 12A and 12B in order to effectively gather the light transmitted through the light guide 12A. Otherwise, a cylindrical lens may be used instead of the transparent pole 14.

What is claimed is:

1. A surface inspection apparatus, comprising:
   an optical scanner irradiating laser light towards a longitudinal inspected object surface moving in a longitudinal direction, and scanning in a widthwise direction of the inspected object surface,
   lens means for converging diffraction light reflected from the inspected object surface, the lens means having a plurality of convex lenses arranged in the widthwise direction of the inspected object surface and adjoining each other,
   spatial filter means, located at the focal plane of the convex lenses for filtering diffraction light converged by the lens means, transmittances within the spatial filter means varying such that quantities of the diffraction light are controlled according to the angle of the diffraction light,
   photoelectric converting means for converting diffraction light from the spatial filter means into electrical signals, and
   partitions, provided between the lens means and the spatial filter means and extending from ends of the lens means and from adjoining portions between adjoining convex lenses towards the spatial filter means in a direction perpendicular to the plane of the convex lenses, for blocking diffraction light which is transmitted through one convex lens and is directed toward portions of the spatial filter means other than portions corresponding to the one convex lens.

2. The surface inspection apparatus of claim 1, wherein the photoelectric converting means includes a plurality of photomultipliers.

3. The surface inspection apparatus of claim 1, wherein the photoelectric converting means includes a plane semiconductor optical sensor.

4. The surface inspection apparatus of claim 1, wherein a light guide is arranged between the spatial filter means and the photoelectric converting means.

5. The surface inspection apparatus of claim 1, wherein a bundle fiber is arranged between the spatial filter means and the photoelectric converting means.

6. The surface inspection apparatus of claim 1, wherein a plurality of bundle fibers are arranged between the spatial filter means and the photoelectric converting means for bundling different diffraction light components.

7. The surface inspection apparatus of claim 1, wherein the spatial filter means includes a light guide with a plurality of light diffusion portions for filtering the diffraction light.

8. The surface inspection apparatus of claim 1, wherein a semi-transparent mirror is arranged above each convex lens, and wherein the surface inspection apparatus also includes first spatial filters for receiving transmission light through the semi-transparent mirror and second spatial filters for receiving light reflected from the semi-transparent mirror.

9. The surface inspection apparatus of claim 1, wherein a semi-transparent mirror is arranged above each convex lens, and a first light guide with a plurality of light diffusion portions is arranged to receive light transmitted through the semi-transparent mirror, and a second light guide with a plurality of light diffusion portions is arranged to receive light reflected from the semi-transparent mirror.

10. The surface inspection apparatus of claim 1, wherein a first light guide with a plurality of light diffusion portions is arranged above the lens means for gathering specific components of diffraction light, and a second light guide with a plurality of light diffusion portions is arranged above the first light guide for gathering diffraction light from the first light guide.

* * * * *